(12) United States Patent
Boday et al.

(10) Patent No.: US 9,081,004 B2
(45) Date of Patent: Jul. 14, 2015

(54) CIRCUIT FOR DETECTING ANALYTES VIA NANOPARTICLE-LABELED SUBSTANCES WITH ELECTROMAGNETIC READ-WRITE HEADS

(75) Inventors: Dylan Joseph Boday, Tucson, AZ (US); Louie Arthur Dickens, Tucson, AZ (US); Steven Mark Groff, Tucson, AZ (US); Icko Eric Timothy Iben, Santa Clara, CA (US); Wayne Alan McKinley, Tucson, AZ (US); Lee Curtis Randall, Tucson, AZ (US); Stephen Leonard Schwartz, Tucson, AZ (US); Anna W. Topol, Jefferson Valley, NY (US); Daniel James Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 1167 days.

(21) Appl. No.: 12/888,408

(22) Filed: Sep. 22, 2010

(65) Prior Publication Data

US 2011/0077869 A1  Mar. 31, 2011

Related U.S. Application Data

(60) Provisional application No. 61/246,329, filed on Sep. 28, 2009.

(51) Int. Cl.
*G01N 33/48* (2006.01)
*G01N 33/543* (2006.01)
*B82Y 15/00* (2011.01)

(52) U.S. Cl.
CPC .......... *G01N 33/54346* (2013.01); *B82Y 15/00* (2013.01); *G01N 33/54326* (2013.01); *G01N 33/54333* (2013.01)

(58) Field of Classification Search
CPC .................. G01N 33/54346; G01N 33/54333; G01N 33/54326; B82Y 15/00
USPC ........................................................... 702/19
See application file for complete search history.

(56) References Cited

U.S. PATENT DOCUMENTS

| 5,005,096 A | 4/1991 | Krounbi et al. |
| 5,146,004 A | 9/1992 | Morris et al. |

(Continued)

OTHER PUBLICATIONS

Liu et al., "Discrimination of specific and non-specific bindings by dielectrophoretic repulsion in on-chip magnetic bio-assays", Journal of Biosensors and Bioelectronics, No. 24, pp. 2294-2297, 2009.

(Continued)

*Primary Examiner* — Sujoy Kundu
*Assistant Examiner* — Steven J Malone
(74) *Attorney, Agent, or Firm* — Cantor Colburn LLP; Bryan Butler (57) ABSTRACT

A circuit for detecting antigens on biosample tracks comprising a processor, an electromagnetic write head for magnetizing nanoparticles attached to the antigens via antibodies in response to a write signal from the processor, and a first amplifier for supplying power to the write head. The circuit further comprises a magneto-resistive read sensor for detecting the magnetized nanoparticles upon receiving a read signal from the processor, and a second amplifier for supplying power to the read sensor. The write head and read sensor may be part of a head module in a magnetic tape drive. Nanoparticles of differing magnetic properties may be selectively paired with antibodies associated with different antigens to allow different antigens to be detected upon a single scan by the read-sensor.

21 Claims, 8 Drawing Sheets

(56) References Cited

U.S. PATENT DOCUMENTS

| | | | |
|---|---|---|---|
| 5,189,571 A | 2/1993 | Murphy et al. | |
| 5,206,159 A | 4/1993 | Cohen et al. | |
| 5,206,590 A | 4/1993 | Dieny et al. | |
| 5,331,493 A | 7/1994 | Schwarz | |
| 5,376,965 A | 12/1994 | Nagasaki et al. | |
| 5,452,164 A | 9/1995 | Cole et al. | |
| 5,465,185 A | 11/1995 | Heim et al. | |
| 5,661,039 A | 8/1997 | Kung et al. | |
| 5,689,384 A | 11/1997 | Albrecht et al. | |
| 5,764,567 A | 6/1998 | Parkin | |
| 5,840,889 A | 11/1998 | Cavalieri et al. | |
| 5,863,507 A | 1/1999 | James | |
| 5,922,537 A * | 7/1999 | Ewart et al. | 435/6.11 |
| 5,948,624 A | 9/1999 | Rothschild et al. | |
| 6,027,946 A | 2/2000 | Weitschies et al. | |
| 6,282,051 B1 | 8/2001 | Albrecht et al. | |
| 6,320,719 B1 | 11/2001 | Albrecht et al. | |
| 6,493,172 B1 | 12/2002 | Morris et al. | |
| 6,643,084 B1 | 11/2003 | Andrew et al. | |
| 6,770,489 B1 | 8/2004 | Enpuku | |
| 6,962,685 B2 | 11/2005 | Sun | |
| 7,342,738 B1 * | 3/2008 | Anderson et al. | 360/77.12 |
| 7,556,863 B2 | 7/2009 | Berning et al. | |
| 2002/0030044 A1 | 3/2002 | Brown | |
| 2002/0119470 A1 | 8/2002 | Nerenberg et al. | |
| 2002/0174453 A1 | 11/2002 | Daniell et al. | |
| 2003/0186465 A1 | 10/2003 | Kraus et al. | |
| 2004/0002125 A1 | 1/2004 | Gombrich et al. | |
| 2004/0061968 A1 | 4/2004 | Fukushima et al. | |
| 2004/0080855 A1 | 4/2004 | Tsuchiya et al. | |
| 2004/0132220 A1 | 7/2004 | Fish | |
| 2004/0166508 A1 | 8/2004 | Pawlak et al. | |
| 2004/0219361 A1 * | 11/2004 | Cui et al. | 428/402.2 |
| 2005/0087000 A1 | 4/2005 | Coehoorn et al. | |
| 2005/0100930 A1 | 5/2005 | Wang et al. | |
| 2006/0040273 A1 | 2/2006 | Chaiken et al. | |
| 2006/0051237 A1 | 3/2006 | Wang et al. | |
| 2006/0128035 A1 | 6/2006 | Coehoorn et al. | |
| 2007/0054154 A1 | 3/2007 | Leu | |
| 2007/0190640 A1 | 8/2007 | Bangert et al. | |
| 2008/0226917 A1 * | 9/2008 | Zhong et al. | 428/403 |
| 2009/0066318 A1 | 3/2009 | Kahlman et al. | |
| 2009/0152657 A1 | 6/2009 | Suh et al. | |
| 2009/0273857 A1 * | 11/2009 | Iben et al. | 360/97.02 |
| 2009/0314066 A1 | 12/2009 | Nieuwenhuis et al. | |
| 2010/0147003 A1 | 6/2010 | Ueda et al. | |
| 2011/0070440 A1 | 3/2011 | Linhardt et al. | |
| 2011/0076726 A1 | 3/2011 | Lakey et al. | |
| 2011/0262955 A1 | 10/2011 | Licher et al. | |
| 2011/0293940 A1 * | 12/2011 | Tokoro et al. | 428/404 |
| 2012/0157330 A1 | 6/2012 | Boday et al. | |
| 2012/0164717 A1 | 6/2012 | Irudayaraj | |

OTHER PUBLICATIONS

Millen et al., "Giant Magenetoresistive Sensors. 2. Detection of Biorecognition Events at Self-Referencing and Magnetically Tagged Arrays", Analytical Chemistry, vol. 80, No. 21, pp. 7940-7946, Nov. 1, 2008.

Osterfeld et al., "Multiplex Protein Assays Based on Real-time Magnetic Nanotag Sensing", Proceedings of the National Academy of Sciences, U S A., vol. 105, No. 52, Dec. 30, 2008.

J. Crowther, "The ELISA Guidebook," Humana Press, Totowa, New Jersey; 2001, pp. 1-425.

P. Fox, et al., "Tear and Serum Antibody Levels in Ocular Herpetic Infection: Diagnostic Precision of Secretory IgA," British Journal of Ophthalmology, 1986, 70, pp. 584-588.

Schuurs et al.,; "Enzyme-Immunoassay", Clini Chim Acta, vol. 81, (1977), pp. 1-40.

* cited by examiner

CIRCUIT FOR DETECTING ANALYTES VIA NANOPARTICLE-LABELED SUBSTANCES WITH ELECTROMAGNETIC READ-WRITE HEADS

CROSS-REFERENCE TO RELATED APPLICATIONS

This application claims the benefit of priority from U.S. Provisional Patent Application Ser. No. 61/246,329, entitled "READ-AFTER-WRITE DETECTION OF ANALYTES VIA NANOPARTICLE-LABELED SUBSTANCES" filed on Sep. 28, 2009, and is related to co-filed, co-pending and commonly assigned US patent application Ser. No. 12/888, 388 entitled "DETECTION OF ANALYTES VIA NANO-PARTICLE-LABELED SUBSTANCES WITH ELECTRO-MAGNETIC READ-WRITE HEADS", Ser. No. 12/888,394 entitled "READ-AFTER-WRITE DETECTION OF ANA-LYTES VIA NANOPARTICLE-LABELED SUB-STANCES", and Ser. No. 12/888,403 entitled "A SERVO CONTROL CIRCUIT FOR DETECTING ANALYTES VIA NANOPARTICLE-LABELED SUBSTANCES WITH ELECTROMAGNETIC READ-WRITE HEADS", all of which are hereby incorporated by reference.

BACKGROUND

The invention relates to analytical devices and processes, and more particularly, to devices and processes that incorporate electromagnetic write-heads and magneto-resistive read-sensors to detect analytes via nanoparticle-labeled substances.

It is known that antibodies bind with antigens as part of the human disease defense system. Presently, antigens are detected by such techniques as immunofluorescence, immunoperoxidase, or enzyme-linked immunosorbent assay (ELISA), each of which then employs a microscope for visual detection of the target antigen. It is desirable to exploit the use of magnetic signaling technology to automate the detection of analytes, such as antigens, and to further apply this technology to the detection of any biological matter.

BRIEF SUMMARY

A first set of antibodies are bonded to a substrate, then this first set of antibodies are exposed to and bonded with target antigens. A second set of antibodies are bonded to demagnetized nanoparticles, and these nanoparticle labeled antibodies are exposed to the target antigens. The nanoparticles are then detected by the use of magneto-resistive read-sensors. Examples of read-sensors include anisotropic magneto-resistive (AMR), giant magneto-resistive (GMR), and tunnel magneto-resistive (TMR) read-sensors.

In an exemplary embodiment of the invention, an electromagnetic write-head first magnetizes the nanoparticles, and then a magneto-resistive read sensor, such as an AMR, GMR, or TMR read-sensor, detects the freshly magnetized nanoparticles.

In another exemplary embodiment, the first set of antibodies may be bonded to biosample tracks deposited on a substrate. The substrate may be a flexible film of polyethylene terephthalate (PET), such as used in conventional magnetic tape, or other polymeric film. Alternately, the substrate may be glass, or may be a Peltier material to allow selective heating and cooling of the substrate and the biological sample on the substrate.

Nanoparticles of differing magnetic properties are selectively paired with antibodies associated with different antigens, so that multiple types of antigens can be simultaneously detected upon a single scan of the read-sensor.

For a fuller understanding of the invention, reference is made to the following detailed description taken in conjunction with the accompanying drawings.

DETAILED DESCRIPTION

The invention is described in exemplary embodiments in the following description with reference to the Figures, in which like numbers represent the same or similar elements. While the invention is described in terms of the best mode for achieving the invention's objectives, it will be appreciated by those skilled in the art that variations may be accomplished in view of these teachings without deviating from the spirit or scope of the invention.

Figure 1:
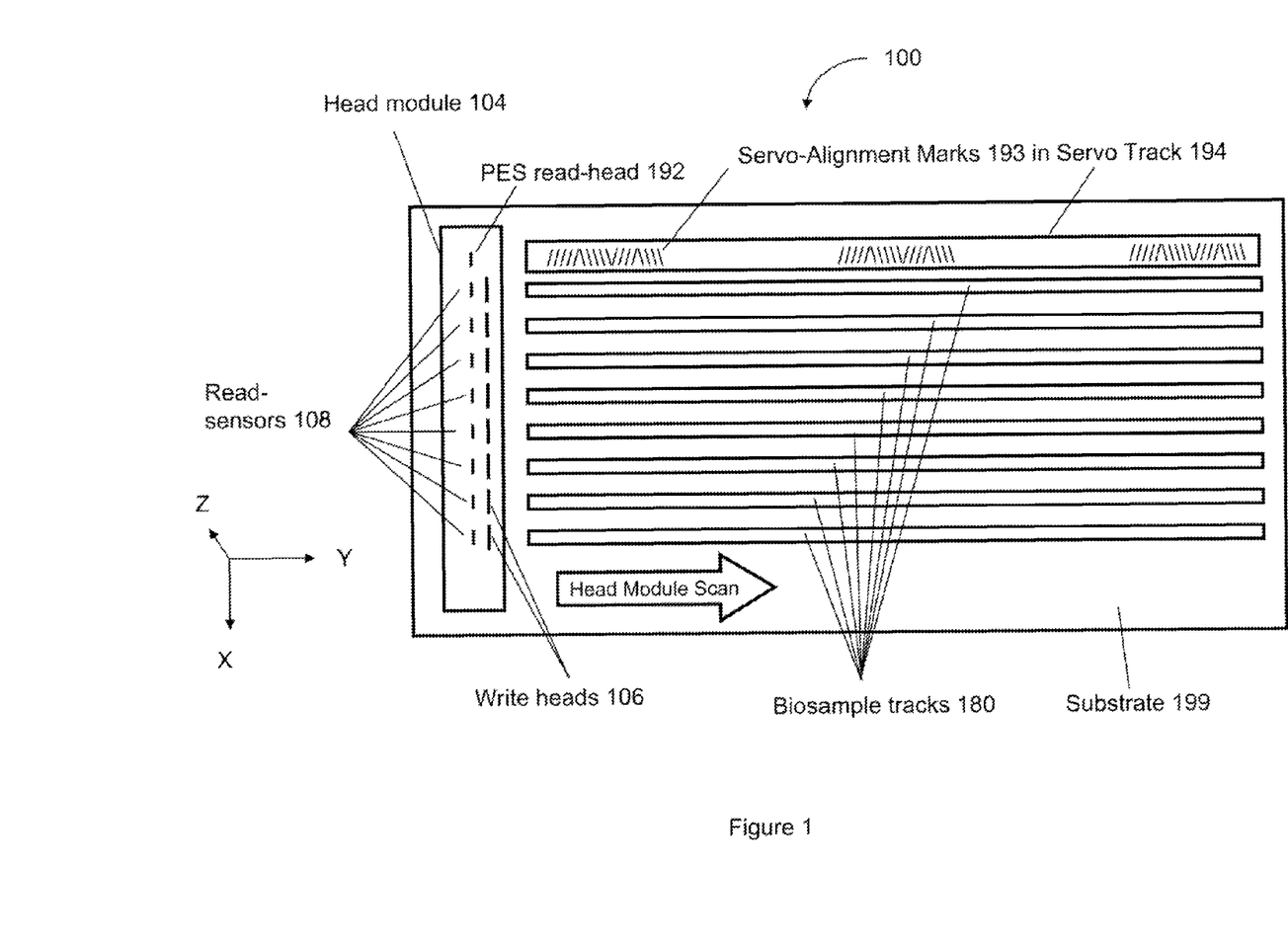
FIG. 1 is a block diagram of a top view of an analytic device according to an exemplary embodiment of the invention.

Referring to FIG. 1, there is illustrated a top view of an example substrate 199, which may comprise a Peltier hard-substrate, a glass substrate, a polyethylene terephthalate (PET, which is commonly known by the trade name of Mylar™) flexible-substrate, or other materials having similar properties. In an exemplary embodiment of the invention, head-module 104 scans across stationary substrate 199 from left-to-right, along the +Y-axis, individually sampling one or simultaneously sampling a plurality of biosample tracks 180. Alternately, substrate 199 may be swept across stationary head-module 104 from right-to-left, along the −Y-axis. If substrate 199 is of a flexible polyethylene terephthalate material, then in one embodiment, this right-to-left motion may be performed as data read-write operations in a magnetic tape drive. As an alternate embodiment of the invention, head-module 104 comprises a helical-scan rotary head-module, and the Y-axis of the biosample tracks 180 is at an angle to the substrate.

FIG. 1 shows electromagnetic write-heads 106 and magneto-resistive read-sensors 108 arranged in pairs in head-module 104. The electromagnetic write-heads 106 first write to biosample tracks 180, and then the adjacent magneto-resistive read-sensors 106 immediately read from biosample tracks 180, which is referred to as a read-after-write operation. In an exemplary embodiment of the invention, substrate 199 comprises eight biosample tracks 180 corresponding to eight bits in a byte, and hence to eight electromagnetic write-head 106 and magnetoresistive read-sensor 108 pairs in a typical head-module 104 used in magnetic tape drive products. However, as alternatives, any number of biosample tracks 180 may be used. The number of electromagnetic write-head 106 and magneto-resistive read-sensor 108 pairs in head-module 104 may be any number ranging from a minimum of one to the number of electromagnetic write-head and magneto-resistive read-sensor pairs in the head-modules of the tape drives. For example, there are sixteen such electromagnetic write-head and magneto-resistive read-sensor pairs in a head module of an IBM 3480™ tape drive. Typically, the number of biosample tracks 180 is an integral multiple of the number of write-head 106 and read-sensor 108 pairs. In an alternate embodiment, a single device may perform the functions of both the write-head 106 and read-sensor 108.

Write-heads 106 may comprise miniature electromagnets, with a coil sandwiched between to poles, such as taught without limitation by U.S. Pat. No. 5,452,164, entitled "Thin Film Magnetic Write-head," which is hereby incorporated by reference in its entirety. Write-heads 106 may comprise other structures with similar functionality.

Read-sensors 108 may be anisotropic magneto-resistive (AMR), giant magneto-resistive (GMR), or tunnel magneto-resistive (TMR) read-sensors, or other devices having similar functionality. AMR read-sensors are taught without limitation by U.S. Pat. No. 5,005,096, entitled "Magnetoresistive Read Transducer Having Hard Magnetic Shunt Bias," which is hereby incorporated by reference in its entirety. AMR read-sensors may comprise other structures having similar functionality. GMR read-sensors, which are also known as spin-valve read-sensors, are taught without limitation by U.S. Pat. No. 5,206,590, entitled "Magnetoresistive Sensor Based On The Spin Valve Effect," which is hereby incorporated by reference in its entirety. GMR read-sensors may comprise other structures having similar functionality. The GMR read-sensors typically have an internal antiparallel pinned layer for increased sensitivity, as taught without limitation by U.S. Pat. No. 5,465,185, entitled "Magnetoresistive Spin Valve Sensor With Improved Pinned Ferromagnetic Layer And Magnetic Recording System Using The Sensor," which is hereby incorporated by reference in its entirety. A recent form of read-sensor, TMR, uses a tunnel barrier layer to augment the GMR internal structure and to provide increased sensitivity, as taught without limitation by U.S. Pat. No. 5,764,567, entitled "Magnetic Tunnel Junction Device With Nonferromagnetic Interface Layer For Improved Magnetic Field Response," which is hereby incorporated by reference in its entirety. TMR read-sensors may comprise other structures having similar functionality.

In the exemplary embodiment illustrated in FIG. 1, write-head 106 is longer along the X-axis direction than read-sensor 108. The active sensing portion of read-sensor 108 is smaller than write-head 106, along the X-axis, as write-head 106 is used to magnetize nanoparticle 212 as described with reference to FIGS. 3 and 4B, for detection of nanoparticles 212 by read-sensor 108. If read-sensor 108 were too large in the X-axis direction, it could potentially encounter unmagnetized nanoparticles 212 and thus register an undesired false-negative detection of antigen 210, as described with reference to FIG. 3.

Head-module 104 may be maintained in linear alignment with biosample tracks 180 along the X-axis by position-error-servo (PES) read-head 192, which reads magnetically encoded servo-alignment marks 193 from servo track 194 on substrate 199. PES read-head 192 may be, for example, an AMR, GMR, or TMR read-sensor. Magnetically encoded servo alignment marks 193 are encoded by the manufacturer of substrate 199 on either a piece of magnetic tape adhered to substrate 199 or encoded on a magnetic recording layer directly deposited on substrate 199. In the example illustrated in FIG. 1, particular servo-alignment marks 193 shown in servo track 194 are Timing Based Servo (TBS) servo-alignment marks such as those used in IBM's Linear Tape Open (LTO) tape drive products, e.g., IBM tape drive models TS1120™ and TS1130™. TBS servo-alignment marks are taught without limitation by U.S. Pat. No. 6,320,719, entitled "Timing Based Servo System for Magnetic Tape Systems," which is hereby incorporated by reference in its entirety. Servo-alignment marks 193 may comprise other structures with similar functionality. The writing of TBS servo-alignment marks 193 in servo track 194, as shown in FIG. 1, is taught without limitation by U.S. Pat. No. 6,282,051, entitled "Timing Based Servo System for Magnetic Tape Systems," which is hereby incorporated by reference in its entirety. TBS servo-alignment marks 193 may comprise other structures with similar functionality.

Figure 2:
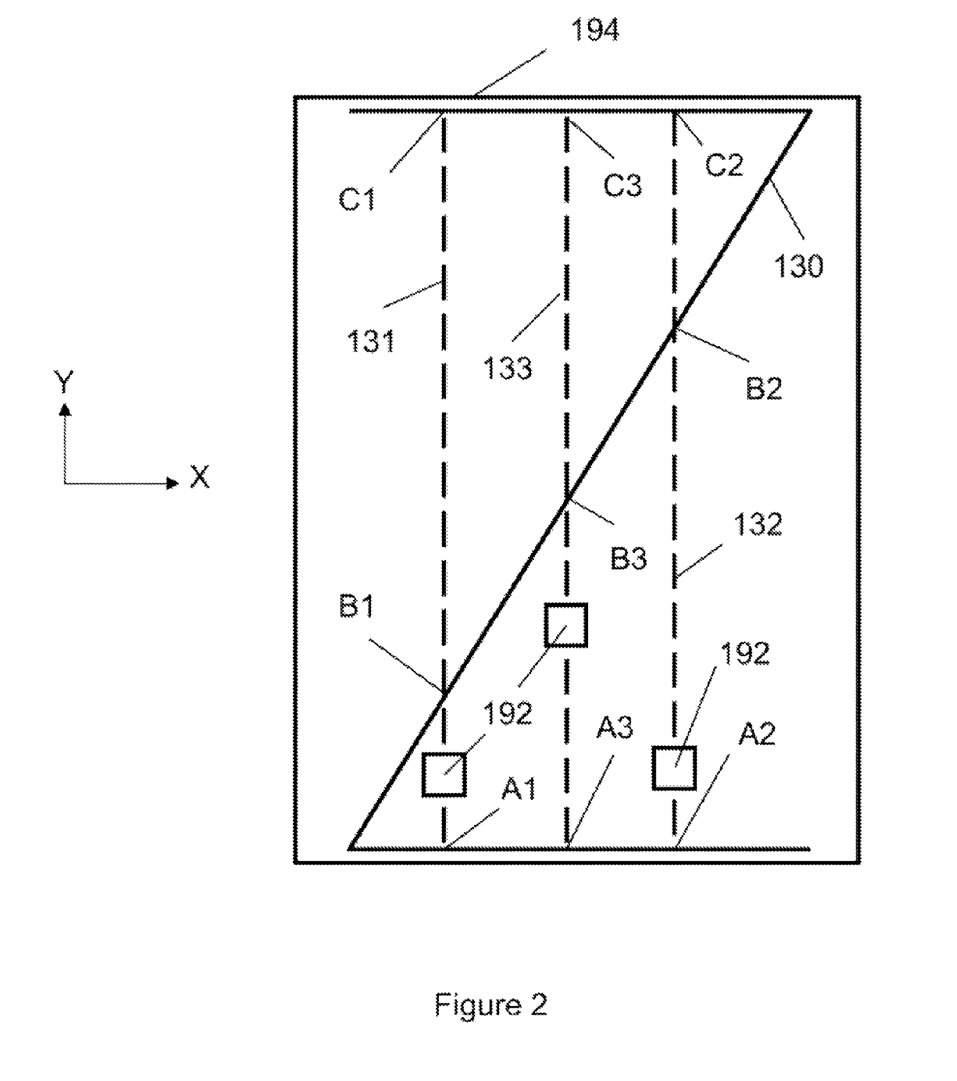
FIG. 2 is a block diagram of an exemplary Z-pattern servo-alignment mark according to an embodiment of the invention.

FIG. 2 illustrates another exemplary embodiment of servo-alignment marks 193 in the form of magnetically-encoded Z-pattern 130 that comprises servo-alignment marks in servo track 194. Relative to the Y-axis, the distance between the top and bottom legs of Z-pattern 130 is constant and equal to the sum of line segments AB and BC, which is equal to the sum of line segments A1B1 and B1C1 in path 131. This distance is also equal to the sum of line segments A2B2 and B2C2 in path 132, and the sum of line segments A3B3 and B3C3 in path 133. Thus, the velocity of head module 104 along the Y-axis relative to substrate 199 may be calculated by dividing the sum of line segments (AB+BC) by the time to transit Z-pattern 130 by head module 104. This velocity calculation is not affected by the position of PES read-head 192 along the X-axis, because the top and bottom of Z-pattern 130 are both parallel to the X-axis.

The position-error-servo (PES) signal corresponding to the position of PES read-head 192, and hence write-heads 106 and read-sensors 108, along the X-axis may be determined by subtracting the distance AB from the distance BC each time a Z-pattern 130 is encountered by PES read-head 192. As can be seen in FIG. 2, the PES signal from PES read-head 192 following path 132 is less than zero because the distance difference (B2C2−A2B2) is less than zero. Similarly, the PES signal from PES read-head 192 following path 131 is greater than zero because the difference (B1C1−A1B1) is greater than zero. Additionally, the value of (BC−AB) varies linearly as PES read-head 192 moves from left to right along the X-axis. Thus the PES signal, as calculated by the difference in distance (BC−AB), provides an X-axis PES signal for head-module 104 and its pairs of electromagnetic write-heads 106 and magneto-resistive read-sensors 108. This PES signal is incorporated into servo control circuit 600 shown in FIG. 6.

In an exemplary embodiment of the invention, the value of the line segment difference (BC−AB) is evaluated based on the time it takes for the PES read head 192 to cross segments AB and BC when the head-module 104 is moving at a constant velocity during its Y-axis seek operation. This is the case where the transit time for the PES read head 192 to cross each Z-pattern 130 is constant. In the exemplary embodiments of the invention shown in FIGS. 1 and 2, TBS servo-alignment marks 193 and Z-pattern 130 could be non-magnetic stripes, either lithographed, silk-screened, or ink-jet printed, and read with an optical laser. In FIG. 2, path 133 is the desired path for PES read-head 192 as electromagnetic write-heads 106 and magneto-resistive read-sensors 108 are aligned with biosample tracks 180. With path 133, the distance difference (B3C3−A3B3) is equal to zero, i.e., line segment B3C3 is equal to line segment A3B3. For path 131, the distance difference (B1C1−A1B1) is greater than zero, which means that head-module 104 must be moved in the +X direction by X-axis actuator 606 so that electromagnetic write-heads 106 and magneto-resistive read-sensors 108 are aligned with biosample tracks 180. The operation of the X-axis actuator 606 is described below with reference to FIG. 6. Similarly, for path 132, the distance difference (B2C2−A2B2) is less than zero, which means that head-module 104 must be moved in the −X direction by X-axis actuator 606 so that electromagnetic write-heads 106 and magneto-resistive read-sensors 108 are aligned with biosample tracks 180.

Figure 3:
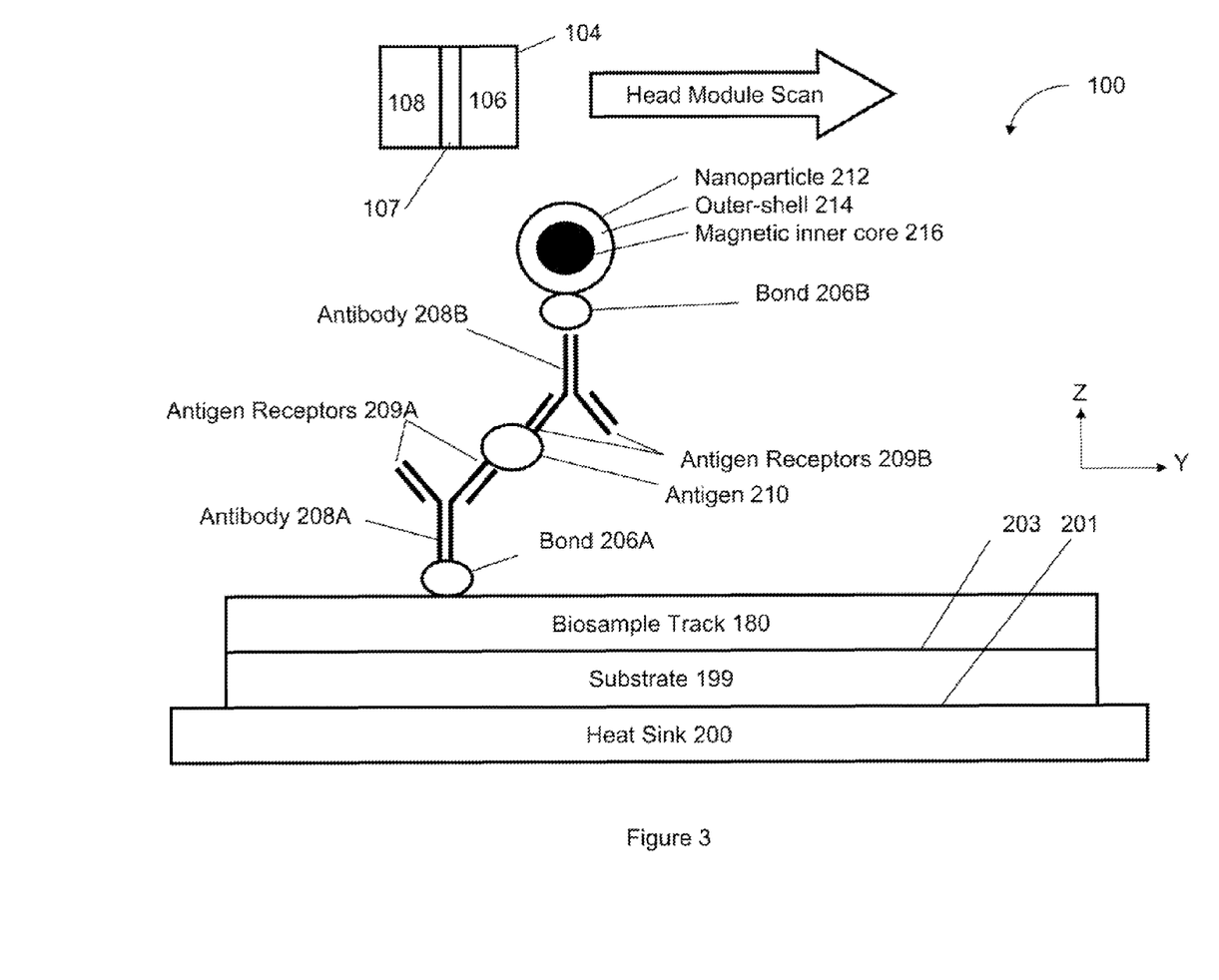
FIG. 3 is a block diagram of a side view of an exemplary analytic device according to an embodiment of the invention.
Figure 4A:
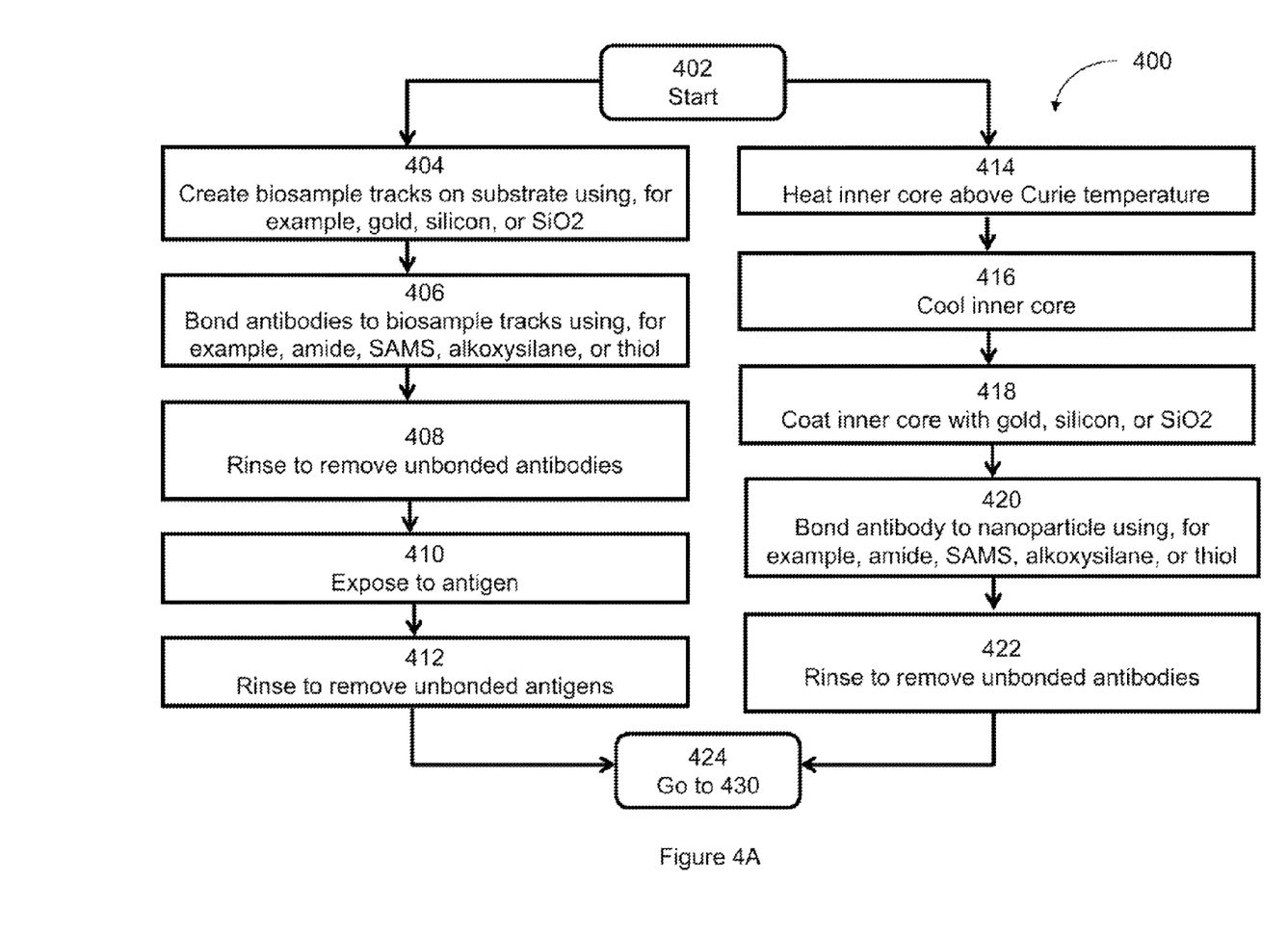
FIG. 4A is a flow chart illustrating an exemplary analytic process according to an embodiment of the invention.
Figure 4B:
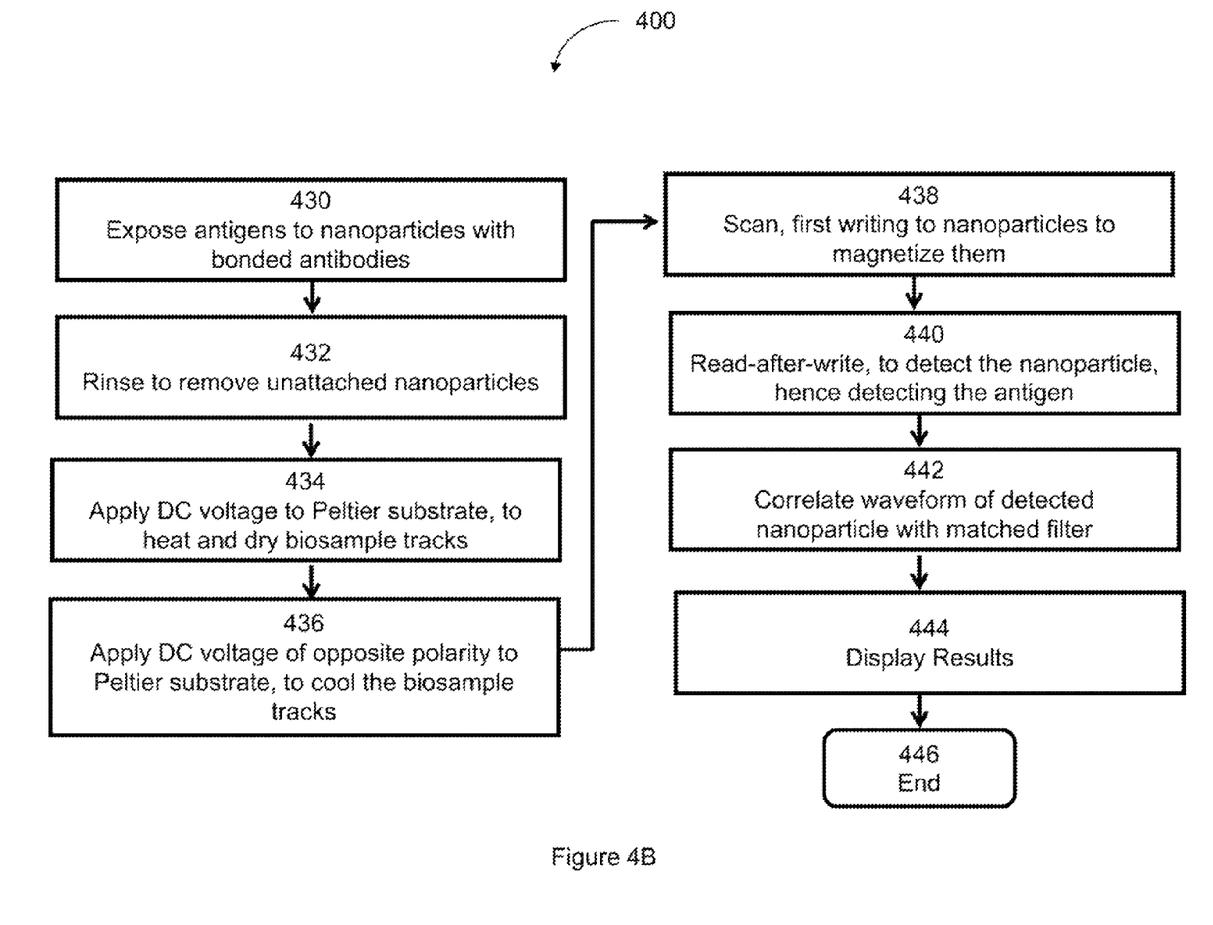
FIG. 4B is a continuation of the flow chart in FIG. 4A, illustrating an exemplary analytic process according to an embodiment of the invention.

FIGS. 1 and 3 illustrate an exemplary analytic device 100, and FIGS. 4A and 4B illustrate an exemplary analytic process 400, respectively. In step 404, biosample tracks 180 are deposited on substrate 199 with nonmagnetic materials such as gold, silicon, or $SiO_2$, and other materials having similar magnetic properties. Deposition methods may include photolithography, silk-screening, and other similar processes. As shown in FIG. 1, biosample tracks 180 are deposited in stripes on substrate 199 with a track-to-track spacing along the X-axis, matching the read-sensor to read-sensor spacing on head-module 104. Then, in step 406, antibodies 208A are bonded to biosample tracks 180, for example, via amide, self-assembled-monolayers (SAMS), alkoxysilane, organic functional trialkoxysilane, or thiol bonds 206A.

In one example of the bonding of the antibodies 208A to the biosample tracks 180, the bonding may comprise first coating substrate 199 with amide, self-assembled-monolayers (SAMS), alkoxysilane, or thiol and then placing a solution of antibodies 208A on substrate 199 and gently rocking substrate 199 for a period of time, up to six hours. Amide refers to organic compounds that contain the functional group consisting of an acyl group, with the chemical notation C=O, linked to a nitrogen (N) atom. A SAM is an organized layer of amphiphilic molecules in which one end of the molecule, the "head group," shows a special affinity for a substrate, such as gold, silicon, or $SiO_2$ biosample tracks 180. At the opposite end of the SAM from the "head group" is a functional group at the terminal end, and it is to this functional group that antibodies 208A are attached in step 406. Lastly, a thiol is a compound that contains the functional group composed of a sulfur atom and a hydrogen atom (—SH). Being the sulfur analog of an alcohol group (—OH), this functional group is referred to either as a thiol group or a mercaptan group.

There are generally five known isotopes (types) of antibodies 208A and 208B for mammals. In FIG. 3, the Y-shape of antibodies 208A and 208B are that of monomer antibodies. There are three isotopes of monomer antibodies: IgD, IgE, and IgG, where the prefix Ig is the symbol for Immunoglobulin. These monomer antibodies each have one unit of Ig. IgD antibodies function mainly as antigen receptors on B cells that have not been exposed to antigens. IgD antibodies have been shown to activate basophils and mast cells to produce antimicrobial factors. B cells are lymphocytes that play a large role in the humoral immune response, as opposed to the cell-mediated immune response, which is governed by T cells. The principal functions of B cells are to make antibodies against antigens, perform the role of Antigen Presenting Cells (APCs) and eventually develop into memory B cells after activation by antigen interaction. B cells are an essential component of the adaptive immune system. IgE antibodies binds to allergens and triggers histamine release from mast cells and basophils, and are involved in allergies. In its four forms, IgG antibodies provide the majority of antibody-based immunity against invading antigens, and thus IgG antibodies are the preferred antibodies 208A and 208B. IgG antibodies are the only antibody capable of crossing the placenta to give passive immunity to fetus.

In an exemplary embodiment of the invention, the base of the stem in a Y-shaped monomer antibody 208A is bonded to biosample tracks 180 via amide, SAMS, alkoxysilane, organic functional trialkoxysilane, or thiol bonds. There is only one isotope of a dimer antibody, IgA, which has two Ig units. IgA antibodies can be found in mucous membrane areas, such as the gut, respiratory track, and urogenital track, as well as in saliva, tears, and maternal milk. Lastly, there is only one isotope of pentamer antibody, IgM, which has five Ig units. IgM antibodies are expressed on the surface of B cells. IgM antibodies eliminate antigens in the early stages of B cell humoral immunity before there are sufficient IgG antibodies in a person's body.

Other analytes may have different antibodies, such as the tetrameric antibody with four Ig units, an example of which is the IgM found in the teleost fish. Thus, analytic process 400 applies to biological analyses in medical and veterinary medicine, as well as to other biological applications. In the exemplary embodiments of the invention, nanoparticles 212 may be bonded to any biological matter and steps in analytic process 400 may be used to track and identify antigens present in a sample of the biological matter.

In the illustrated embodiment of analytic process 400, step 408 comprises rinsing substrate 199 with water such as distilled water or other rinsing agent, which may have its surface tension reduced via a very mild surfactant such as a mild detergent solution. The rinsing removes any antibodies 208A that are not specifically bonded to analytic tracks 180. After rinse step 408, antibodies 208A are exposed to antigens 210 in step 410. In one example, this may be accomplished by placing a blood sample or other biological sample on substrate 199 and then gently rocking substrate 199 for a period of time, up to six hours. Antigens 210 may comprise cancer cells, viruses such as Human Papilloma Virus (HPV), or bacteria. Human Papilloma Virus can lead to infections and cancers of the human reproductive organs. Antibodies 208A are specifically chosen based on the targeted antigens 210.

In step 410, antigens 210 are bonded to monomer antibodies 208A at antigen receptors 209A which are diagrammatically shown to be at the v-shaped end of antibodies 208A. Each monomer antibody 208A has two antigen receptors 209A. Step 410 may include repetitive rocking of substrate 199 to facilitate the bonding of antigens 210 and antibodies 208A at antigen receptors 209A. Then, in step 412, another rinse is performed on substrate 199 with water such as distilled water or other rinsing agent, which may have its surface tension reduced via a very mild surfactant such as a mild detergent solution. Step 412 is analogous to step 408, but this time for removing antigens 210 not bonded to antibodies 208A.

In parallel with steps 404, 406, 408, 410, 412 is the creation of nanoparticle-labeled antibodies in steps 414, 416, 418, 420, and 422 of the illustrated analytic process. In step 414, magnetic inner cores, shown as inner core 216 in FIG. 2, may be heated above their Curie temperature to demagnetize the inner cores. The demagnetization keeps the nanoparticles that comprise the inner cores as individual particles by mitigating the forming of lumps which magnetized nanoparticles are prone to form. Magnetic inner cores 216 may comprise hard magnetic materials with high coercivity, such as $Fe_2O_3$, $CrO_2$, and Barium Ferrite BaFe. As examples, magnetic inner cores 216 may comprise iron oxide based nanoparticle materials, including M Fe$_2$O$_4$ (where M may be Co, Ni, Cu, Zn, Cr, Ti, Ba, or Mg) nanomaterials, and iron oxide coated nanoparticle materials or other structures with similar functionality. The forming of such nanoparticles is taught without limitation by U.S. Pat. No. 6,962,685, entitled "Synthesis of Magnetite Nanoparticles and the Process of Forming," which is hereby incorporated by reference in its entirety. Then, in step 416, the heated magnetic inner cores 216 are allowed to cool. Steps 414 and 416 are optional steps, as the manufacture of inner cores 216, which may include high temperature sintering, may render inner cores 216 demagnetized during the manufacturing process.

Following step 416, step 418 may comprise coating inner cores 216 with an outer-shell 214, for example, of nonmagnetic gold, silicon, or SiO$_2$, to create nanoparticles 212. The step of coating the inner cores 216 with outer-shells 214 is analogous to creating biosample tracks 180 in step 404. Then, in step 420, antibodies 208B are bonded to nanoparticles 212 via amide, self-assembled-monolayers (SAMS), alkoxysilane, organic functional trialkoxysilane, or thiol bonds 206B. This bonding is analogous to bonding antibodies 208A to biosample tracks 180 in step 406. The bonding of the antibodies 208B may be accomplished by first coating nanoparticles 212 with amide, self-assembled-monolayers (SAMS), alkoxysilane, organic functional trial koxysilane, or thiol and then placing nanoparticles 212 in a solution containing antibodies 208B and gently rocking this solution for a period of time, up to six hours. Antibodies 208A and 208B are biologically identical, as both bond to the same antigen 210. Following step 420, step 422 comprises rinsing nanoparticles 212 with water, such as distilled water, or other rinsing agent, which may have its surface tension reduced via a very mild surfactant such as a mild detergent solution to remove unbonded antibodies. The rinsing step 422 is analogous to the rinsing step 408 above. At the conclusion of both steps 412 and 422, process 400 converges at step 424 and continues with step 430 in FIG. 4B.

In step 430, antigens 210 are exposed to nanoparticles 212 which have antibodies 208B bonded to them. This may be done by placing a solution of nanoparticle-labeled antibodies 208B on substrate 199 and then gently rocking substrate 199 for a period of time, up to six hours. Antigen receptors 209B of antibodies 208B bond with antigen 210. Step 432 comprises rinsing substrate 199 with water, such as distilled water, or other rinsing agent, which may have its surface tension reduced via a very mild surfactant such as a mild detergent solution. The rinsing in step 432 removes any nanoparticles 212 not bonded to an antigen 210 and is analogous to step 408. If substrate 199 is a Peltier substrate, in optional step 434, a DC voltage of a first polarity may be applied to the Peltier substrate, to heat surface 208 and hence dry both biosample tracks 180 and biological sample 206A-208A-210-208B-206B-212. Then, in optional step 436, a DC voltage of a second and opposite polarity, may be applied to the Peltier substrate, to cool surface 203 and hence cool both biosample tracks 180 and biological sample 206A-208A-210-208B-206B-212. Heat sink 200 may be used to dissipate excess heat generated by the Peltier substrate along surface 201.

In the exemplary embodiment of the analytical process of the invention shown in FIG. 4B, scan step 438 involves moving head-module 104 linearly in the +Y direction relative to substrate 199, which could equally be done by moving substrate 199 linearly in the −Y direction relative to head-module 104. In previous step 414, inner cores 216 were demagnetized. Now, in step 438, write-head 106 writes to nanoparticles 212 to magnetize inner cores 216. Write-head 106 may write with a constant "DC" magnetic polarity for the duration of scan steps 438 and 440, so that there are no unwritten regions of substrate 199. Then in read-after-write step 440, read-sensor 108 detects the freshly magnetized inner cores 216 of nanoparticles 212, and hence detecting antigens 210 because nanoparticles 212 are bonded to antibodies 208B, which in turn are bonded to antigens 210. The adjacent logical-steps 438 and 440, as well as the physical proximity of write-head 106 and read-sensor 108 in a typical electromagnetic head module, provide an advantage when using tape drive products to detect antigens. The inner cores 216 of nanoparticles 212 are magnetized by write-head 106 along the Y-axis, in what is called longitudinal-recording in the tape drive industry. This is the same direction that read-sensor 108 magnetically detects nanoparticles 212. As a result, the nanoparticles 212 may be magnetized by write-head 106 and then magnetically detected by read-sensor 108 in the same scan of the biosample tracks 180. Magnetic shield 107 separates write-head 106 and read-sensor 108 so that there is no meaningful cross-talk between write-head 106 and read-sensor 108 during steps 438 and 440.

As an alternate embodiment of the invention, once steps 438 and 440 are completed by moving head-module 104 linearly in the +Y direction relative to substrate 199, write-head 106 may be turned off as nanoparticles 212 are now magnetized. Step 440 may be repeated multiple times across biosample tracks 180 along both the +Y and −Y directions during which read-sensor 108 repeatedly checks for magnetized nanoparticles 212 and hence detecting antigens 210. The multiple read operations insure that all antigens 210 on biosample tracks 180 are detected. As described above with reference to FIG. 1, the antigens 210 are attached to nanoparticles 212 through antibodies 208A and 208B.

In another exemplary embodiment of the invention where there are more biosample tracks 180 than write-head 106 and read-sensor 108 pairs in head-module 104, head-module 104 may scan the biosample tracks 180 in a serpentine pattern. The head-module 104 performs a scan in the +Y direction, as head-module 104 only provides read-after-write capability in the +Y direction as illustrated in FIG. 1. Then a second head-module comprising a mirror image of head-module 104 may perform a read-after-write operation in the −Y direction.

The coercivity of a magnetic inner core 216 may be selectively chosen to have any of various values, depending upon the antigen 210 to be detected. The nanoparticles 212 with magnetic inner cores 216 of different coercivity values may be respectively bonded to different types of antibodies 208A and 208B to detect a various types of antigens 210 on the substrate 199 at the same time. A nanoparticle 212 thus may have different magnetic properties associated with each antigen-antibody combination. Read-sensor 108 detects the different magnetic properties of inner core 216 based on different materials used for that inner core, for example, Fe$_2$O$_3$, CrO$_2$, BaFe, M Fe$_2$O$_4$ (where M may be Co, Ni, Cu, Zn, Cr, Ti, Ba, or Mg), or other structures with similar functionality. Read-sensor 108 thus could detect different antigens 210 on the same scan of the biosample tracks 180, per steps 438 and 440 in FIG. 4B. To facilitate the detection of nanoparticles of different magnetic properties and hence the detection of different types of antigens, calibration of read-sensor 108 may be performed according to an exemplary calibration process 500 illustrated in FIG. 5.

Calibration of Read-Sensors

Figure 5:
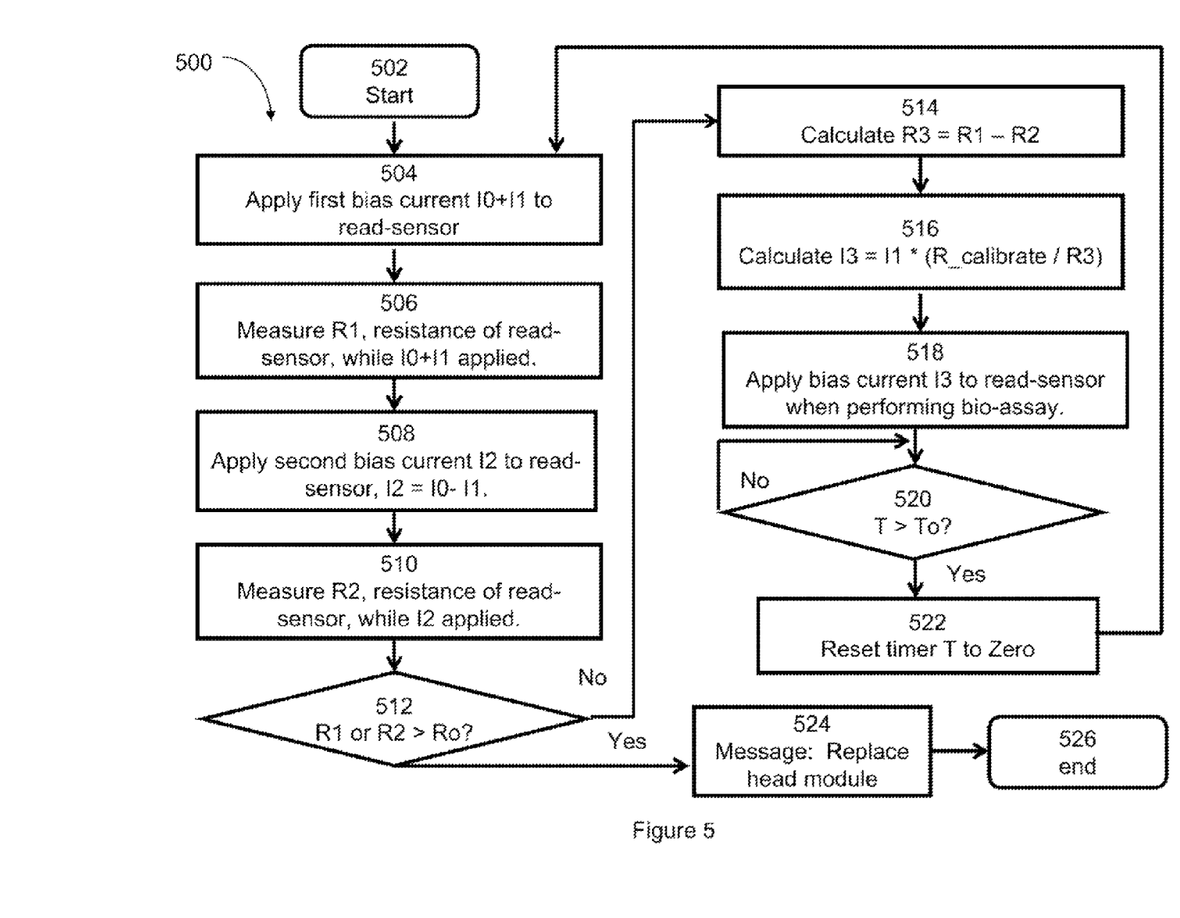
FIG. 5 is a flow chart illustrating an exemplary process for calibrating a read-sensor for use in detecting nanoparticle labeled antigens, according to an embodiment of the invention.

Referring to FIG. 5, in one exemplary embodiment of the calibration of read-sensor 108, calibration process 500 begins at step 502 and proceeds with step 504, where a first "DC"

bias current (I0+I1) is applied to read-sensor 108. This first bias current may consist of an offset DC current I0 plus a DC current I1. In succeeding step 506, the process 500 measures resistance R1 of read-sensor 108 while DC current (I0+I1) is applied. In step 508, second DC bias current I2 may be applied to read-sensor 108, where I2=I0−I1. In steps 506 and 508, offset current I0 is typically zero milliamperes, but may have a positive or negative value. In succeeding step 510, the calibration process 500 measures resistance R2 of read-sensor 108 while DC current I2 is applied, where I2=I0−I1. Then in step 512, a determination is made whether resistance R1 or R2 exceeds threshold resistance R0 and thus indicating a non-operational read-sensor 108. If resistance R1 or R2 exceeds the threshold, then process 500 branches to step 524 where a message is displayed to the user to replace head-module 104 as the read-sensor 108, which is an integral part of head-module 104, may be non-operational. If neither resistance R1 nor resistance R2 exceeds the threshold per the determination in step 512, then process 500 branches to step 514 and calculates resistance R3, where R3=R1−R2.

Figure 7:
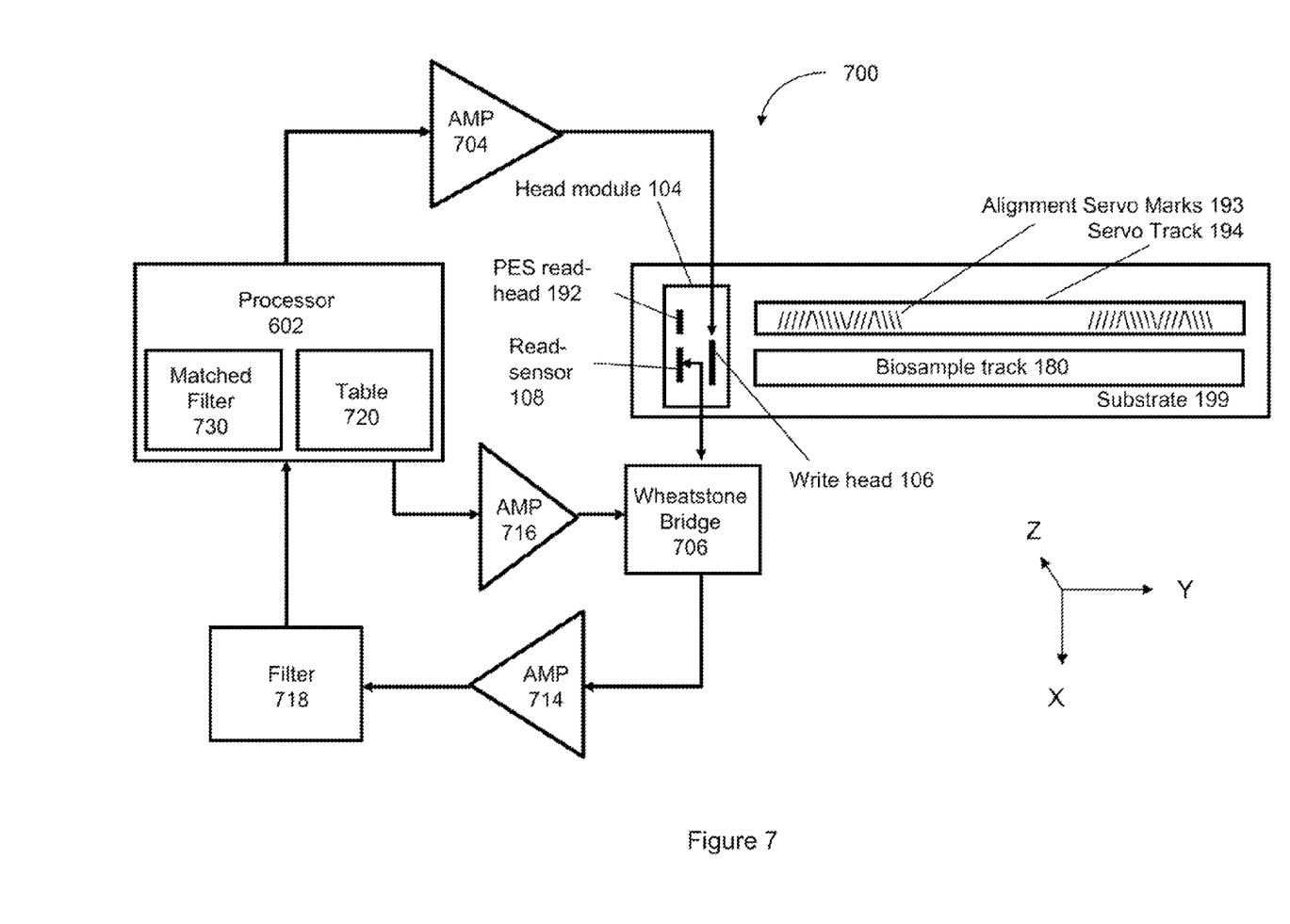
FIG. 7 is a block diagram of an exemplary write and read circuit for use with an analytic device, according to an embodiment of the invention.

In step 516, calibration process 500 calculates a bias current I3, where I3=I1*(R_calibrate/R3) and R_calibrate is a preset value maintained by processor 602 shown in FIG. 7. In step 518, calibration process 500 applies bias current I3 to read-sensor 108 when performing step 440 as part of the bio-assay process 400. In step 520, a determination is made whether calibration time T exceeds a time threshold T0, where T is the time elapsed during the calibration steps 504 to 518. If time T has not exceeded the threshold T0, then calibration process 500 cycles back to step 520 and continues checking time T against the threshold T0. Otherwise, process 500 resets time T to zero in step 522 before returning to step 504 to begin the calibration process again. Process 500 is executed by processor 602, as described below with reference to FIG. 7.

Mitigation of Corrosion in Head-Module

When read-sensor 108 is not in use for detecting magnetized nanoparticles 212, in one exemplary embodiment of the invention, a current may be passed through read-sensor 108 in order to mitigate corrosive effects of ambient air. This current may be, for example, a direct current in the range of three to seven milliamperes. Alternately, the current may be a pulse-width-modulated (PWM) direct current or alternating current (AC) having an amplitude of, for example, three to seven milliamperes. This current causes read-sensor 108 to be sufficiently warm to minimize corrosive effects of water vapor, chlorine, and other gases present in ambient air in the vicinity of the biosample tracks 180. In one exemplary embodiment of the invention, this current may be applied based on signals sent by processor 602 to a power amplifier 716, as illustrated in FIG. 7. The power amplifier 716 supplies electric power to Wheatstone Bridge 706, where read-sensor 108 is a component of the Wheatstone Bridge 706.

Read-sensor 108 is essentially an impedance device, such as a resistor, which exhibits a change in resistance when exposed to a magnetic field. In the illustrated exemplary embodiment of the calibration, process 500 assumes that read-sensor 108 responds linearly when not saturated by the applied magnetic field, and to a first order approximation, read-sensor 108 does respond linearly. Correlation coefficients of up to 99.9% have been empirically measured, regarding the change in resistance in read-sensor 108 versus applied magnetic field, indicating a sufficiently high degree of linearity for application of calibration process 500.

Per Ohm's law, V=IR, voltage and current are directly proportional to each other in read-sensor 108. Thus, as an alternate embodiment of calibration process 500, first and second voltages V1, V2 could be used to obtain the first resistance R1 and second resistance R2, respectively, without loss of generality.

A Servo Control Circuit

Figure 6:
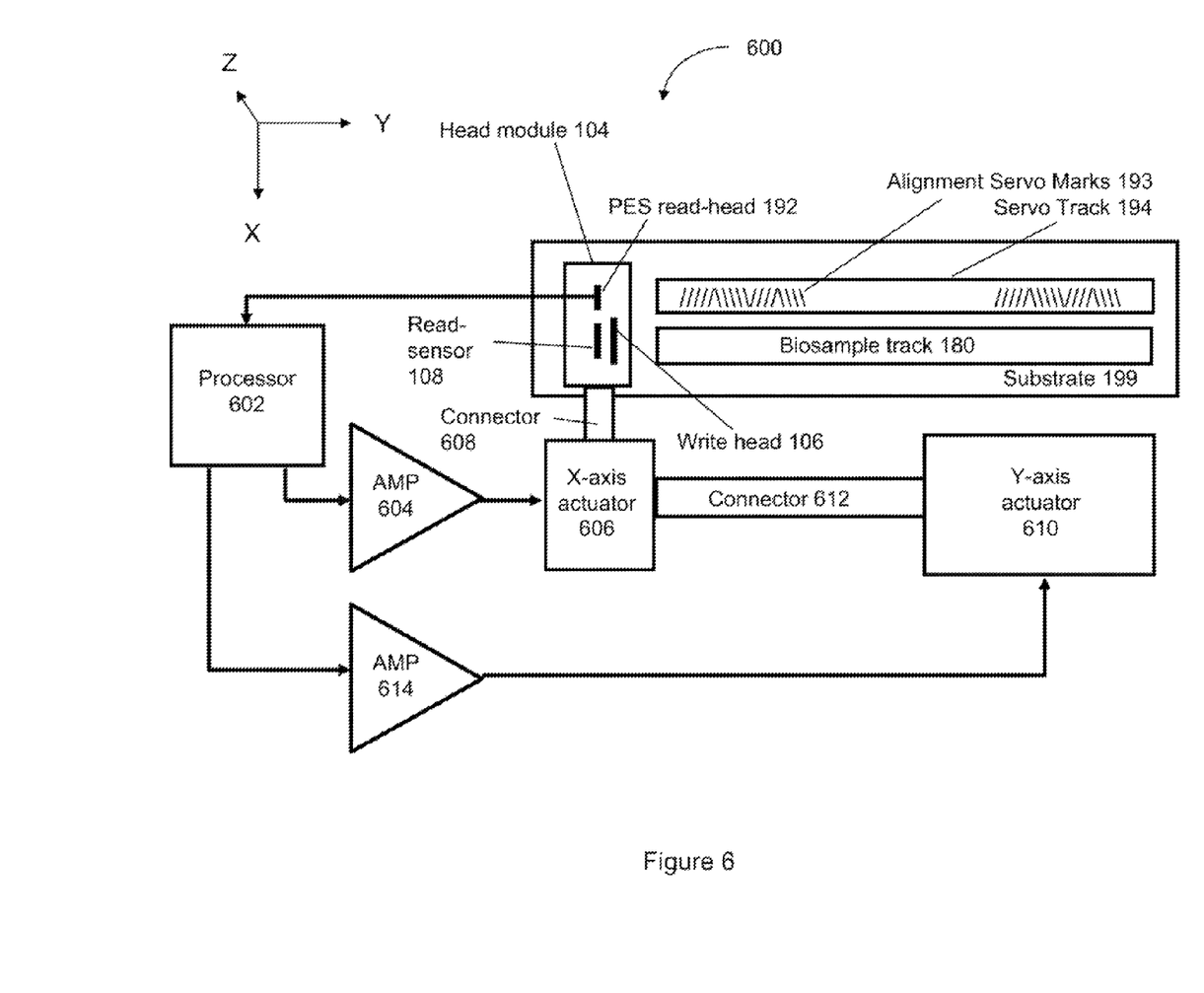
FIG. 6 is a block diagram of an exemplary circuit for controlling the X-axis and Y-axis motion of the head-module of an analytic device, according to an embodiment of the invention.

FIG. 6 shows an exemplary embodiment of a servo control system 600 for controlling the X-axis and Y-axis motion of head-module 104. As an example, FIG. 6 shows one bio-sample track 180, and one pair of write-head 106 and read-sensor 108. Processor 602 receives position-error-servo (PES) signals from PES read-head 192 when PES read-head 192 reads servo-alignment marks 193 in servo track 194. Based on this PES information, processor 602 sends a signal to power amplifier 604 to control X-axis actuator 606 which in turn controls the motion of head module 104 in the X-axis direction. With X-axis actuator 606 connected to head-module 104 via mechanical connector 608, head-module 104 may be positioned to center write-head 106 and read-sensor 108 on biosample track 180. Processor 602 may send signals to power amplifier 614 to control Y-axis actuator 610 for conducting a scan by head module 104 across substrate 199. With Y-axis actuator 610 connected to X-axis actuator via mechanical connector 612, head-module 104 can be moved along the Y-axis in a controllable manner.

As an example, when a predetermined number of servo-alignment marks 193 are read by PES read-head 192, processor 602 stops the Y-axis motion of head-module 104. A servo-system for control of X-axis actuator 606 and head-module 104 along the X-axis direction, particular to servo-alignment marks 193 shown in servo track 194 in FIG. 1, is taught without limitation by U.S. Pat. No. 5,689,384, entitled "Timing Based Servo System for Magnetic Tape System," which is hereby incorporated by reference in its entirety. The servo-system may comprise other structures with similar functionality. As previously described regarding Z-pattern 130, the velocity of head module 104 relative to substrate 199 along the Y-axis can be calculated by dividing distance AB+BC by the time it takes for head module 104 to transit Z-pattern 130. This velocity measurement can be used by processor 602 to control Y-axis actuator 610 to keep head module 104 at a constant Y-axis velocity Vy relative to substrate 199. The position along the Y-axis of head module 104 relative to substrate 199 can be obtained by counting servo-alignment marks 193 or Z-pattern 130 by PES read-head 192 and processor 602.

A Write and Read Circuit

FIG. 7 shows an exemplary embodiment of a write and read circuitry 700 for writing to the biosample tracks 180 (i.e., for magnetizing nanoparticles 212) and reading from the biosample tracks 180 (i.e., for sensing and detecting the magnetized nanoparticles 212). Processor 602 may send signals to power amplifier 704 which provides power to write-head 106 for magnetizing nanoparticles 212. Processor 602 may further send signals to power amplifier 716 which powers Wheatstone bridge 706. Read-sensor 108 is one component in Wheatstone bridge 706 and thus receives DC current from Wheatstone bridge 706. Wheatstone bridge 706 serves the function of balancing out the zero-magnetism resistance of read-sensor 108 so that only the change in resistance of read-sensor 108 is passed onto amplifier 714. Such resistance change is due to the detection of a magnetized nanoparticle 212, which is sent to amplifier 714 and filter 718 before being received by processor 602.

Filter 718 filters out 60 Hz noise, which is pervasive noise in an office or laboratory with lighting where processes of the invention are typically performed. Processor 602 makes the determination of whether a nanoparticle 212 was detected, and hence an antigen 210 being detected. The change in resistance of read-sensor 108 is directly proportional to the magnetic field provided by nanoparticle 212, which may have different coercivities depending upon whether inner core 216 is $Fe_2O_3$, $CrO_2$, BaFe, M $Fe_2O_4$ (M=Co, Ni, Cu, Zn, Cr, Ti, Ba, Mg), etc. In addition, particular antibodies 208A and 208B could be associated with inner cores 216 of nanoparticles 212 having a given coercivity. As a result, processor 602 could register the detection of different antigens 210 during steps 438 and 440 of process 400 depending on corresponding combinations of antibodies 208A and 208B and nanoparticles 212. The identification of the various antigens 210 simultaneously on the same biosample track 180 may be facilitated by a lookup table 720 in processor 602. In one exemplary embodiment of the invention, the lookup table 720 contains a list of (a) antigens 210, (b) the antibodies 208A and 208B used for bonding antigens and nanoparticles, and (c) the coercivity of the inner cores 216 of nanoparticles 212 bonded to the antibodies 208B.

Correlation of Detection Results

In another embodiment of the invention, a correlation calculation may be performed by the write and read circuit of FIG. 7 to improve the accuracy of the detection of magnetized nanoparticles 212. Referring to FIGS. 3, 4A, 4B, 6 and 7, processor 602 performs correlation calculation C(y) in equation [1] between a detection signal profile g(y) read by read-sensor 108 when a nanoparticle 212 is detected and a matched filter. The matched filter comprises an impulse response h(y) of an ideal signal profile of a detected nanoparticle. Since h(y) is used repetitively, it may be calculated once and stored as matched filter 730 in processor 602. In equation [1], η is the integration variable along the Y-axis as read-sensor 108 scans along the Y-axis.

$$C(y)=\int g(\eta)h(\eta-y)d\eta \qquad \text{Equation [1]}$$

The range of correlation C(y) is between −1 and +1, where +1 represents the ideal correlation of one hundred percent (100%). The electrical waveform g(y) of each potential detection of a nanoparticle 212 by read-sensor 108 has its correlation C(y) calculated in step 442 of FIG. 4A. Processor 602 then compares this correlation C(y) against a threshold correlation value C0 before accepting the signal g(y) as a valid detection of a nanoparticle 212. This correlation removes spurious electrical noise from actual detections of nanoparticles, and thus mitigates false-positive detections of antigens. In step 444 of FIG. 4B, the results of a scan may be displayed to a physician or clinician to inform the physician or clinician of the presence (or absence) of target antigens in the biological sample. The results may include items such as the antigen(s) tested for, the types of antibodies used, a simple positive-detection or negative-detection indication for each antigen, the number of nanoparticles counted for each antigen to give an indication of the prevalence of the targeted antigen, and the number of rejected detections based on the correlation calculation of step 442. In addition, the results may include patient name, date of test, time of test, and name of attending doctor or clinician. Process 400 ends at step 446 in FIG. 4B.

Those of skill in the art will understand that changes may be made with respect to the exemplary embodiments described above, including, but not limited to, changes to the ordering of the steps. Further, those of skill in the art will understand that differing specific component arrangements may be employed than those illustrated herein.

While the exemplary embodiments of the invention have been illustrated and described in detail, it should be apparent that modifications and adaptations to those embodiments may occur to one skilled in the art without departing from the scope of the invention.

What is claimed is:

1. A circuit for detecting nanoparticle-labeled antigens on a biosample track, comprising:
    a processor;
    a write head configured to move linearly along the biosample track for magnetizing nanoparticles attached to the antigens upon receiving a write signal from the processor;
    a first amplifier for supplying power to the write head;
    a read sensor configured to move along the biosample track with the write head for detecting the magnetized nanoparticles attached to the antigens upon receiving a read signal from the processor;
    a second amplifier for supplying power to the read sensor; and
    a position-error servo read head configured to control a motion of the write head and read sensor along the biosample track by reading a Z-pattern on a servo track aligned with the biosample track.

2. The circuit of claim 1, further comprising a Wheatstone bridge for balancing out zero-magnetism resistance of the read sensor, the read sensor being a component of and receiving a current from the Wheatstone bridge.

3. The circuit of claim 1, further comprising a filter coupled to the processor and the read amplifier for filtering out electrical noise to improve the accuracy of the antigen detection.

4. The circuit of claim 1, wherein the nanoparticles comprise inner cores having different magnetic properties respectively corresponding to different antigen types, and the circuit detects the different antigen types simultaneously.

5. The circuit of claim 4, wherein the processor identifies the different antigen types based on a table comprising the antigen types and the corresponding magnetic properties of the inner cores.

6. The circuit of claim 5, wherein the antigens are labeled with the nanoparticles via antibodies, and the table includes information on the antibodies and the coercivity of the inner cores.

7. The circuit of claim 1, wherein the read sensor repeatedly senses the magnetic presence of a particular nanoparticle to improve the accuracy of the antigen detection.

8. The circuit of claim 1, wherein the processor performs a result correlation in response to the read sensor detecting a particular nanoparticle to improve the accuracy of the antigen detection.

9. The circuit of claim 8, wherein the result correlation includes a calculation to remove spurious electrical noise from the detection of the particular nanoparticle.

10. The circuit of claim 8, wherein the result correlation is based on an ideal signal profile of a detected magnetized nanoparticle.

11. The circuit of claim 10, wherein the result correlation comprises:
    calculating an impulse response for the ideal signal profile;
    calculating a correlation between a read sensor signal on the detection of the particular nanoparticle and the impulse response; and
    accepting the signal as a valid detection if the calculated correlation meets a threshold.

12. The circuit of claim 1, wherein the second amplifier applies a current of about three to seven milliamperes to the read sensor to mitigate corrosive effects of ambient air when the read sensor is not used for detecting the antigens.

13. The circuit of claim 12, wherein the current comprises a pulse-width-modulated (PWM) direct current having an amplitude of about three to seven milliamperes.

14. The circuit of claim 12, wherein the current comprises an alternating current (AC) having an amplitude of about three to seven milliamperes.

15. The circuit of claim 12, wherein the second amplifier applies the current to the read sensor in response to a signal from the processor.

16. The circuit of claim 1, wherein the read sensor is calibrated for detecting different target antigens on the biosample track.

17. The circuit of claim 16, wherein the calibration comprises:
 measuring a resistance R1 of the read sensor while a first biased current (I0+I1) is applied to the read sensor, wherein I0 is an offset direct current and I1 is a direct current;
 measuring a resistance R2 of the read sensor while a second bias current (I0−I1) is applied to the read sensor;
 indicating that the read sensor is non-operational if any of the resistances R1 and R2 exceeds a threshold;
 otherwise, calculating a bias current I3=I1*(R_calibrate/R1+R2), where R_calibrate is a preset value, and applying the bias current I3 to the read sensor while scanning the biosample track.

18. The circuit of claim 17, wherein the resistances R1 and R2 are measured while respectively applying different voltages V1 and V2 to the read sensor.

19. The circuit of claim 16, wherein the calibration is repeated as long as a time threshold has not been exceeded.

20. A system for detecting nanoparticle-labeled antigens, comprising:
 a biosample track deposited on a magnetic tape media and having the nanoparticle-labeled antigens attached thereon;
 an electromagnetic write head configured to move linearly along the biosample track for writing to the tape media to magnetize the nanoparticles;
 a magneto-resistive read sensor configured to move along the biosample track with the write head for reading the tape media to detect the antigens via the nanoparticles;
 a circuit comprising a processor for controlling the write-head and read-sensor, a write amplifier for supplying power to the write head, and a read amplifier for supplying power to the read sensor and
 a position-error servo read head configured to control a motion of the write head and read sensor along the biosample track by reading a Z-pattern on a servo track aligned with the biosample track.

21. The system of claim 20, wherein the write head and read sensor are part of a head module, and the head module and the circuit are part of a magnetic tape drive.

* * * * *